United States Patent [19]

Inoue et al.

[11] Patent Number: 5,425,919
[45] Date of Patent: Jun. 20, 1995

[54] TOTAL ORGANIC CARBON ANALYZER

[75] Inventors: Keiji Inoue, Suita; Youzo Morita, Kameoka, both of Japan

[73] Assignee: Shimadzu Corporation, Kyoto, Japan

[21] Appl. No.: 35,298

[22] Filed: Mar. 22, 1993

[30] Foreign Application Priority Data

Mar. 26, 1992 [JP] Japan .................................. 4-101717

[51] Int. Cl.$^6$ .............................................. G01N 7/08
[52] U.S. Cl. ........................................ 422/67; 422/78; 436/146

[58] Field of Search .......................... 422/67, 68.1, 78; 436/143, 145, 146

[56] References Cited

PUBLICATIONS

WPI Acc No.:90-078828/11.

*Primary Examiner*—Lyle A. Alexander
*Attorney, Agent, or Firm*—Oliff & Berridge

[57] ABSTRACT

A purgeable organic carbons analyzer for measuring the content of purgeable organic carbons (POC) in a water sample using barium hydroxide as the $CO_2$ absorbing agent in a $CO_2$ absorber.

5 Claims, 2 Drawing Sheets

TOTAL ORGANIC CARBON ANALYZER

The present invention relates to a TOC analyzer and a POC analyzer which measure the content of total organic carbons (TOC) and purgeable organic carbons (POC) in a water sample.

BACKGROUND OF THE INVENTION

A growing need exists to measure the total content of organic carbons (OC) in public waters, such as river water, etc., or in industrial waste waters. A conventional method of measuring the content of total organic carbons (TOC) in a water sample is as follows. First, the sample is pre-processed to eliminate inorganic carbons (IC). That is, an inorganic acid, such as hydrochloric acid or sulfuric acid, is added to the sample, and, as shown in FIG. 1A, a high purity air from an air cylinder 11 is blown into the sample 10 to convert the inorganic carbons to $CO_2$ and purge the $CO_2$ out of the sample 10.

After the pre-processing, the sample 10 is sent to a TC combustion tube 15, where the sample 10 is heated to a high temperature (i.e., combusted) and all of the carbon included in the sample 10 is converted to $CO_2$. The combustion gas is sent to a non-dispersive infrared gas analyzer (NDIR) 21 in (FIG. 1B,) where the amount of $CO_2$ in the gas is measured. The controller 22 of the total organic carbons analyzer calculates the TOC content of the sample 10 from the amount of $CO_2$ measured by the NDIR 21 and the amount of sample 10 sent to the TC combustion tube 15.

There is a problem in pre-processing sample 10 to purge out the inorganic carbons. When the high purity air is blown into the sample 10, purgeable organic carbons (POC) are also purged out of the sample 10. Thus, in the above method, the content of purgeable organic carbons must be measured separately to measure the correct total organic carbons content. In order to measure the POC content, a purgeable organic carbons analyzer 17 is incorporated in the TOC analyzer, as shown in FIG. 1A.

The operation of a POC analyzer can be understood referring to FIG. 2. First, the same amount of sample 10 as sent to the TC combustion tube 15 in the above measurement is sent to a purger 27. Then high purity air is passed through the sample 10 by injecting the gas in the bottom of purger 27. The amount of high purity air injected into the purger 27 is the same as that blown into the sample 10 in the above described pre-processing step, whereby the same amount of purgeable organic carbons as purged from the sample 10 in the pre-processing is purged out from the sample 10 in the purger 27. The purgeable organic carbons content of the sample 10 can then be obtained by sending the gas from the purger 27 to the TC combustion tube 15 in the TOC analyzer.

There is another problem in the above method. Because part of the inorganic carbons (IC) is purged out of sample 10 as $CO_2$ when the high purity air is injected into the sample 10 in purger 27 as, it is necessary to eliminate $CO_2$ before the gas from the purger 27 is sent to the TC combustion tube 15 in order to measure the correct content of purgeable organic carbons. Thus a $CO_2$ absorber 28 is provided in the POC analyzer 17, as shown in FIG. 2.

SUMMARY OF THE INVENTION

Conventional $CO_2$ absorbers use lithium hydroxide as the $CO_2$ absorbing agent contained in the $CO_2$ absorber 28. However, when esters (which are purgeable organic carbons) are included in the purgeable organic carbons purged out of sample 10 (i.e., when esters are included in the sample 10 as organic carbons), the esters react with and are trapped by the lithium hydroxide, and the correct POC content cannot be measured.

The present invention addresses the problem and provides a POC analyzer, and hence a TOC analyzer, that can measure the correct content of purgeable organic carbons and total organic carbons in of a water sample. According to the present invention, a POC analyzer for measuring the content of purgeable organic carbons in a water sample comprises:

a sample container for containing the water sample;

a blower for blowing purging gas into the water sample in the sample container to purge out purgeable organic carbons where the inorganic carbons are converted to $CO_2$ and also purged out;

a $CO_2$ absorber containing $CO_2$ absorbing agent including barium hydroxide for absorbing $CO_2$ in the gas from the sample container; and a heater for heating the $CO_2$ absorbing agent in the $CO_2$ absorber.

Barium hydroxide is very weak in its ability to decompose esters compared to lithium hydroxide, while it has the same ability to absorb $CO_2$ as lithium hydroxide. Thus, esters in purgeable organic carbons purged out of the water sample in the sample container are hardly trapped by the $CO_2$ absorbing agent in the $CO_2$ absorber, and by measuring the carbon content of the gas that has passed through the $CO_2$ absorber, the correct content of purgeable organic carbons including esters is obtained. Since such abilities of barium hydroxide are properly realized when it is heated to 30°–80 ° C., preferably 40°–60° C., a heater is provided.

A TOC analyzer according to the present invention measures the total content of organic carbons in a water sample with i) a POC measuring stage for measuring POC and ii) a TOC measuring stage for measuring total organic carbons without purgeable organic carbons. The TOC analyzer of the present invention comprises:

a sample vessel for holding the water sample;

a purging gas source for providing a purging gas;

a combustion tube for combusting the water sample or gas to convert the carbons included therein to $CO_2$;

a sample container for containing the water sample;

a $CO_2$ absorber containing $CO_2$ absorbing agent including barium hydroxide for absorbing $CO_2$ in the gas from the sample container;

a $CO_2$ analyzer for measuring the amount of $CO_2$ in the gas received from the combustion tube;

a heater for heating the $CO_2$ absorbing agent in the $CO_2$ absorber;

a sample flow controller for, in the POC measuring stage, sending the sample water in the sample vessel to the sample container, and for, in the TOC measuring stage, sending the water sample in the sample vessel to the combustion tube; and a gas flow controller for, in the POC measuring stage, sending the purging gas in the purging gas source to the water sample in the sample container and for, in the TOC measuring stage, sending the purging gas to the water sample in the sample vessel.

Details of the TOC analyzer including other features and variations of the present invention are explained in the following description of the preferred embodiment.

DETAILED DESCRIPTION OF A PREFERRED EMBODIMENT

Figure 1A:
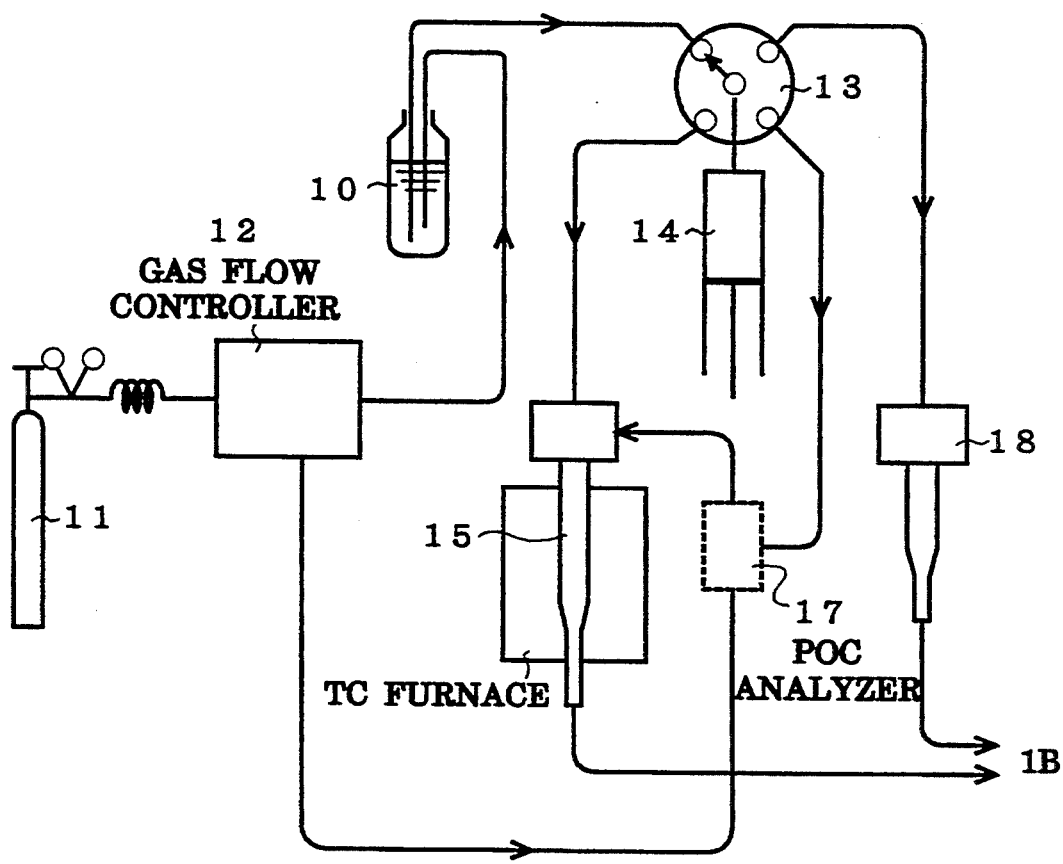
FIG. 1A is a diagram of the first part of the sample and gas circuit of a TOC analyzer.
Figure 1B:
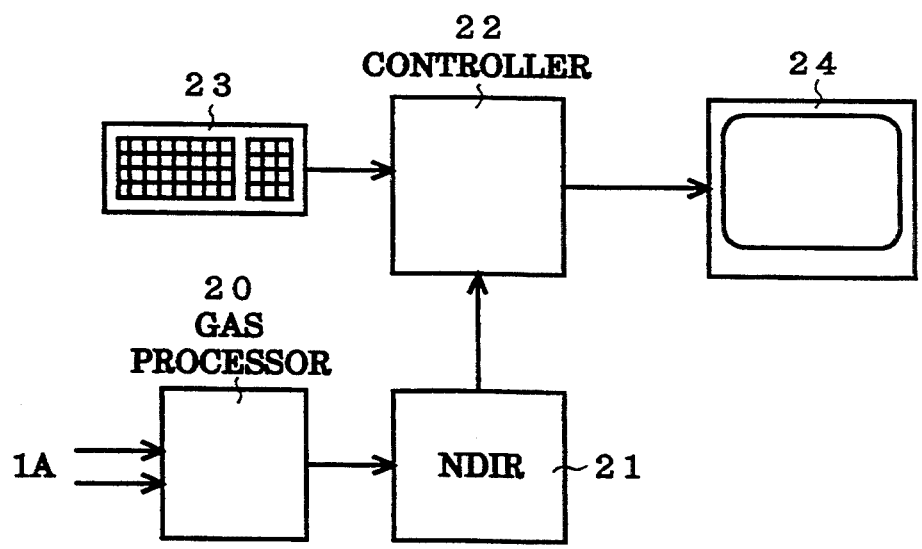
FIG. 1B is a diagram of the second part of the circuit and a control part of the TOC analyzer.
Figure 2:
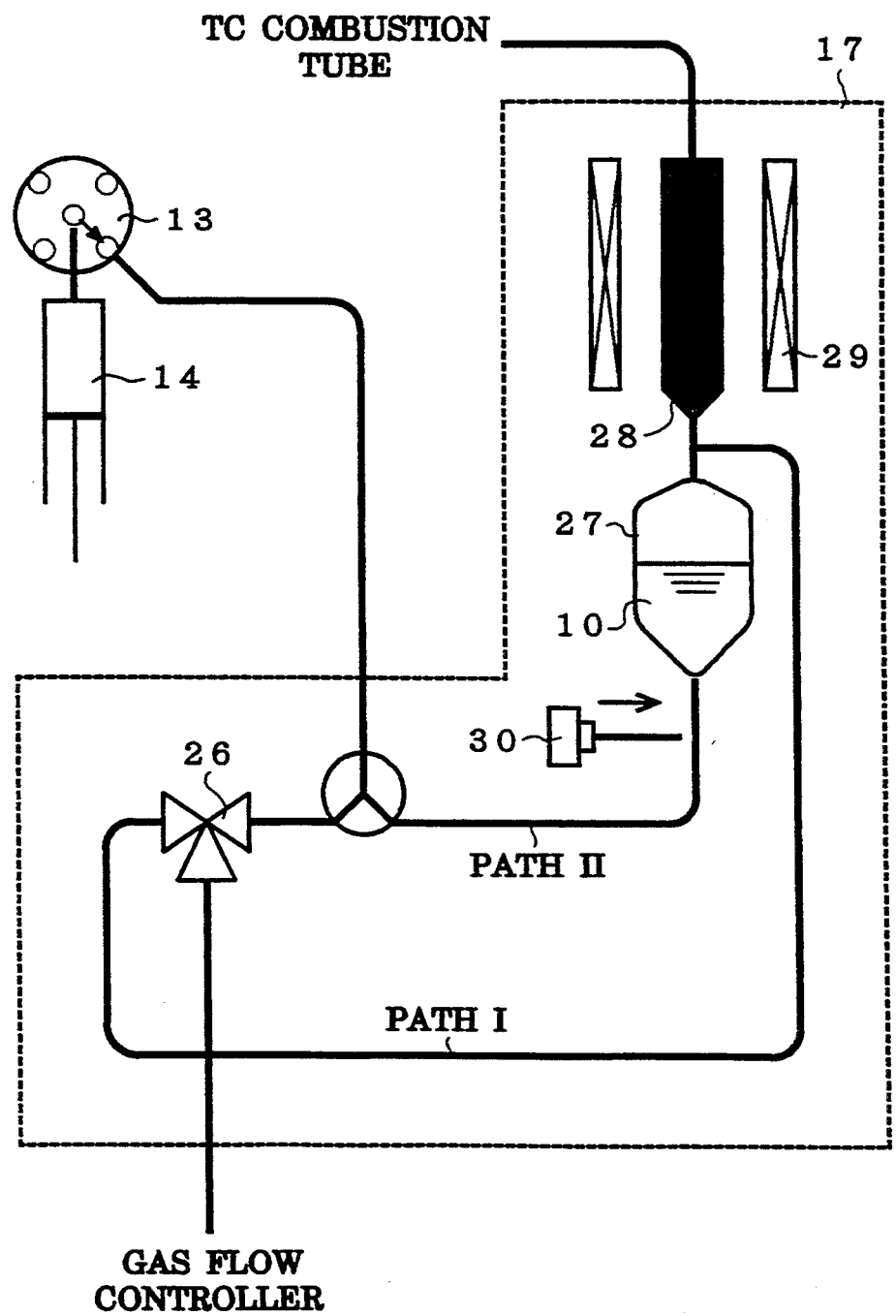
FIG. 2 is a circuit diagram of a POC analyzer.

A TOC analyzer including a POC analyzer according to the present invention is described referring to FIGS. 1A, 1B and 2. In the present embodiment, the $CO_2$ absorber 28 uses, instead of lithium hydroxide (LiOH) used in the conventional analyzer, crystalline barium hydroxide ($Ba(OH)_2 \cdot 8H_2O$) as the $CO_2$ absorbing agent. And, in order to make the $CO_2$ absorbing agent (barium hydroxide) function properly, a heater 29 surrounding the $CO_2$ absorber 28 is provided (no heater is provided in conventional POC analyzers). The TOC analyzer of the present embodiment includes, besides the POC analyzer 17: a sample vessel for reserving a water sample 10; a gas cylinder 11 containing high purity air; a gas flow controller 12 for controlling the flow of the high purity air; a rotary valve 13 and a syringe 14 for controlling the flow of the sample 10; a TC combustion tube 15 for heating the sample 10 from the syringe 14 or gas from the POC analyzer 17 to a high temperature to convert all the carbon content to $CO_2$; a pre-measurement gas processor 20 for dehumidifying and conditioning the gas from the TC combustion tube 15; an NDIR 21 for measuring the amount of $CO_2$; and a controller with a keyboard 23 and a display 24. An IC reactor 18 is also provided in the TOC analyzer of the present embodiment for measuring the IC content of the sample 10.

First the purgeable organic carbons analyzer 17, as shown in FIG. 2, is used to measure the purgeable organic carbons content of the water sample 10. When the POC analyzer 17 of the present embodiment is used, the $CO_2$ absorber 28 is heated to 30°–80° C., preferably 40°–60° C., by the heater 29. Then a proper amount of the sample 10 is sucked by the syringe 14 (FIG. 1A), and, by turning the rotary valve 13 and an electromagnetic valve 26 of the POC analyzer 17 (FIG. 2) to the path I, the sample 10 is sent to the purger 27. After turning the valve 26 to the path II, a predetermined amount of high purity air metered by the gas flow controller 12 (FIG. 1A) is injected into the sample 10 in the purger 27, through the bottom of purger 27. By the air injection, the purgeable organic carbons included in the sample 10 are purged out, and some part of the inorganic carbons in the sample 10 is also purged out as $CO_2$. The gas from the purger 27 passes through the $CO_2$ absorber 28 where the $CO_2$ in the gas is trapped but no purgeable organic carbons are is trapped in the POC analyzer 17 of the present embodiment. After passing through the $CO_2$ absorber 28, the gas is sent to the TC combustion tube 15 in FIG. 1A, where the gas is heated to a high temperature, whereby all the carbon in the gas from the purger 27 is oxidized to become $CO_2$. The combustion gas from the TC combustion tube 15 is sent via the pre-measurement gas processor 20 to the NDIR 21 in FIG. 1B, where the amount of $CO_2$ in the combustion gas is measured. Referring to the amount of the sample 10 sent to the purger 27, the controller 22 calculates the purgeable organic carbons (POC) content of the sample 10.

After (or before) the POC content is measured, the total organic carbons (TOC) content is measured. First, the sample is pre-processed to eliminate the inorganic carbons, as described above. That an inorganic acid, such as hydrochloric acid or sulfuric acid, is added to the sample 10 and the same amount of high purity air as injected into the sample 10 in the purger 27 is blown by the gas flow controller 12 into the sample 10 to purge out the inorganic carbons as $CO_2$. Here, purgeable organic carbons is also purged out of the sample 10, but whose amount is already correctly known using the POC analyzer 17 as described above.

After the pre-processing, the sample 10 is sucked by the syringe 14 and then, by turning the rotary valve 13, sent to the TC combustion tube 15, where the sample 10 is combusted and all of the carbon included in the sample is converted to $CO_2$. The combustion gas is sent, via the pre-measurement gas processor 20, to the NDIR 21, where the amount of $CO_2$ in the combustion gas is measured. The amount of $CO_I$ measured here corresponds to the total organic carbons in the sample 10 but does not include the purgeable organic carbons purged out in the pre-processing step. Thus, the correct total organic carbons content is calculated by adding the content of purgeable organic carbons measured above to the total organic carbons content measured here.

EXAMPLE

An experiment on the ester absorbing efficiency of barium hydroxide and lithium hydroxide is performed. Each of the $CO_I$ absorbing agents is contained in the $CO_2$ absorber 28, and methyl acetate, ethyl acetate, and vinyl acetate gases are passed through the $CO_2$ absorber 28 respectively utilizing a septum 30 used in a gas chromatograph. When the barium hydroxide is used as the $CO_2$ absorbing agent in the $CO_2$ absorber 28, the $CO_2$ absorber 28 is heated by the heater 29 to 40° C. The ester absorbing efficiencies of the agents for the respective ester gases are listed in Table 1. As shown in Table 1, barium hydroxide has a much smaller absorbing efficiency of ester gases than lithium hydroxide. Thus, the $CO_2$ absorber according to the present invention using barium hydroxide as the $CO_2$ absorbing agent passes almost all of the purgeable organic carbons purged from the sample 10 and the correct purgeable organic carbons content can be measured.

TABLE 1

| POC | Ester absorbing efficiency | |
|---|---|---|
|  | $Ba(OH)_2$ | LiOH |
| Methyl Acetate | 1.8% | 34.0% |
| Ethyl Acetate | 0.8% | 37.7% |
| Vinyl Acetate | 23.3% | 48.5% |

What is claimed is:

1. A purgeable organic carbons analyzer for measuring the content of purgeable organic carbons in a water sample, comprising:

a sample container for containing the water sample;

a blower for bubbling purging gas through the water sample in the sample container to convert inorganic carbons in the water sample to $CO_2$ and purge purgeable organic carbons and $CO_2$ out of the water sample;

a $CO_2$ absorber containing a $CO_2$ absorbing agent including barium hydroxide for absorbing $CO_2$ in the purged gas received from the sample container;

a heater for heating the $CO_2$ absorbing agent in the $CO_2$ absorbing agent in the $CO_2$ absorber;

a combustion tube for combusting gas that is not absorbed by the $CO_2$ absorber, to convert purgeable organic carbons in the gas to $CO_2$; and a $CO_2$ analyzer for measuring the content of purgeable organic carbons in the water sample based on the amount of $CO_2$ in the combusted gas received from the combustion tube.

2. The purgeable organic carbons analyzer according to claim 1, wherein the $CO_2$ absorbing agent is crystalline barium hydroxide ($Ba(OH)_2 \cdot 8H_2O$).

3. A total organic carbons analyzer for measuring the total content of organic carbons in a water sample, comprising:

a sample vessel for holding the water sample;

a sample container for containing a predetermined portion of the water sample;

a sample flow controller for sending the predetermined portion of the water sample in the sample vessel to the sample container and the remainder of the water sample in the sample vessel to a combustion tube;

a purging gas source for providing a purging gas;

a gas flow controller for sending the purging gas from the purging gas source to the sample container and the sample vessel to purge purgeable organic carbons and $CO_2$;

a $CO_2$ absorber containing a $CO_2$ absorbing agent including barium hydroxide for absorbing $CO_2$ in the purged gas received from the sample container;

a heater for heating the $CO_2$ absorbing agent in the $CO_2$ absorber;

a combustion tube for combusting the water sample from the sample vessel and gas that is not absorbed by the $CO_2$ absorber; and a $CO_2$ analyzer for measuring the total content of organic carbons in the water sample based on the amount of $CO_2$ contained in combusted gases received from the combustion tube.

4. The total organic carbons analyzer according to claim 3, wherein the $CO_2$ absorbing agent is crystalline barium hydroxide ($Ba(OH)_2 \cdot 8H_2O$).

5. The total organic carbons analyzer according to claim 3, wherein the $CO_2$ analyzer is a non-dispersive infrared gas analyzer.

* * * * *